US011315662B2

(12) United States Patent
Clinton et al.

(10) Patent No.: US 11,315,662 B2
(45) Date of Patent: Apr. 26, 2022

(54) ASSAY INFORMATION MANAGEMENT METHODS AND DEVICES

(71) Applicant: Meso Scale Technologies, LLC., Rockville, MD (US)

(72) Inventors: Charles M. Clinton, Clarksburg, MD (US); Xinri Cong, Germantown, MD (US); Eli N. Glezer, Del Mar, CA (US); Sudeep Kumar, Hackettstown, NJ (US); Carl Stevens, Silver Spring, MD (US); Michael Vock, Loveland, OH (US); Jon S. Willoughby, Potomac, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 214 days.

(21) Appl. No.: 16/594,301

(22) Filed: Oct. 7, 2019

(65) Prior Publication Data
US 2020/0035333 A1   Jan. 30, 2020

Related U.S. Application Data

(60) Continuation of application No. 14/862,298, filed on Sep. 23, 2015, now Pat. No. 10,446,263, which is a division of application No. 12/844,345, filed on Jul. 27, 2010, now abandoned.

(60) Provisional application No. 61/271,873, filed on Jul. 27, 2009.

(51) Int. Cl.
| | |
|---|---|
| *G01N 35/00* | (2006.01) |
| *G16C 20/20* | (2019.01) |
| *G01N 33/543* | (2006.01) |
| *B01L 3/00* | (2006.01) |
| *G16H 10/40* | (2018.01) |
| *G01N 33/53* | (2006.01) |

(52) U.S. Cl.
CPC ............ *G16C 20/20* (2019.02); *B01L 3/54* (2013.01); *G01N 33/54306* (2013.01); *G01N 35/00663* (2013.01); *G16H 10/40* (2018.01); *B01L 2300/02* (2013.01); *G01N 2035/00633* (2013.01); *G01N 2035/00851* (2013.01)

(58) Field of Classification Search
CPC ..... B01L 3/54; B01L 3/50; B01L 3/00; G16C 20/20; G16C 20/00; G16H 10/40; G16H 10/00; G01N 33/54306; G01N 33/543; G01N 33/53; G01N 33/50; G01N 35/00663; G01N 35/00613; G01N 35/00594; G01N 35/00584
USPC .............. 436/50, 43; 422/502, 501, 500, 50
See application file for complete search history.

(56) References Cited

U.S. PATENT DOCUMENTS

| | | | |
|---|---|---|---|
| 5,641,634 A | 6/1997 | Mandecki | |
| 6,217,744 B1 * | 4/2001 | Crosby | ............ G01N 33/48785 |
| | | | 205/775 |
| 7,858,321 B2 | 12/2010 | Glezer et al. | |
| 2002/0078016 A1 | 6/2002 | Lium et al. | |
| 2002/0154815 A1 | 10/2002 | Mizutani | |
| 2003/0113713 A1 | 6/2003 | Glezer et al. | |
| 2003/0231986 A1 | 12/2003 | Kocher | |
| 2004/0022677 A1 | 2/2004 | Wohlstadter et al. | |
| 2004/0087008 A1 | 5/2004 | Schembri | |
| 2004/0189311 A1 | 9/2004 | Glezer et al. | |
| 2005/0009122 A1 | 1/2005 | Whelan et al. | |
| 2005/0118468 A1 | 6/2005 | Adams et al. | |
| 2005/0205673 A1 | 9/2005 | Morris et al. | |
| 2005/0240352 A1 | 10/2005 | Liang | |
| 2006/0199196 A1 | 9/2006 | O'Banion et al. | |
| 2006/0210435 A1 | 9/2006 | Alavie et al. | |
| 2006/0216203 A1 | 9/2006 | Fuller et al. | |
| 2007/0004030 A1 | 1/2007 | Ogura et al. | |
| 2007/0237678 A1 | 10/2007 | Roesicke et al. | |
| 2008/0024301 A1 | 1/2008 | Fritchie et al. | |
| 2008/0138889 A1 | 6/2008 | Noda et al. | |
| 2008/0164210 A1 | 7/2008 | DeMarco | |
| 2008/0189163 A1 | 8/2008 | Rosenberg et al. | |
| 2008/0284602 A1 | 11/2008 | Morris et al. | |
| 2009/0042734 A1 | 2/2009 | Yoshida et al. | |
| 2009/0066507 A1 | 3/2009 | Lewington et al. | |
| 2009/0090874 A1 | 4/2009 | Roper et al. | |
| 2009/0269242 A1 | 10/2009 | Nozawa | |
| 2011/0022331 A1 | 1/2011 | Clinton et al. | |

(Continued)

FOREIGN PATENT DOCUMENTS

| | | |
|---|---|---|
| CN | 1549921 A1 | 11/2004 |
| CN | 101046849 A | 10/2007 |

(Continued)

OTHER PUBLICATIONS

European Examination Report dated Mar. 26, 2020 received in European Patent Application No. 10 806 878.4.

(Continued)

*Primary Examiner* — Christine T Mui
(74) *Attorney, Agent, or Firm* — Scully, Scott, Murphy & Presser, P.C.

(57) ABSTRACT

The present invention relates to methods, devices and systems for associating assay information with an assay consumable used in a biological assay. Provided are assay systems and associated consumables, wherein the assay system includes a reader adapted to read/erase/write information from/to an assay consumable identifier associated with the assay consumable. Various types of assay information are described, as well as methods of using such information in the conduct of an assay by an assay system.

28 Claims, No Drawings

(56) References Cited

U.S. PATENT DOCUMENTS

2012/0145778 A1  6/2012  Cong et al.
2016/0012208 A1  1/2016  Clinton et al.

FOREIGN PATENT DOCUMENTS

| | | |
|---|---|---|
| EP | 1 760 471 B1 | 3/2007 |
| EP | 1 767 948 A2 | 3/2007 |
| JP | 2003-216846 A | 7/2003 |
| JP | 2004-20563 A | 1/2004 |
| JP | 2004-163427 A | 6/2004 |
| JP | 2006-250928 A | 9/2006 |
| JP | 2007-71554 A | 3/2007 |
| JP | 2007-148876 A | 6/2007 |
| JP | 2008-516209 A | 5/2008 |
| JP | 2009-2952 A | 1/2009 |
| WO | 2006/040083 A1 | 4/2006 |
| WO | 2006/060125 A2 | 6/2006 |
| WO | 2006/101229 A1 | 9/2006 |
| WO | 2008/076374 A2 | 6/2008 |
| WO | 2009/006523 A2 | 1/2009 |

OTHER PUBLICATIONS

Summons to Attend Oral Proceedings dated Mar. 19, 2021 received in European Patent Application No. 10 806 878.4.
Australian Patent Examination Report dated May 27, 2014 received in Australian Patent Application No. 2010281480.
Canadian Examination Report dated Jan. 28, 2019 received in Canadian Patent Application No. 2,769,378.
Canadian Examination Report dated Jan. 31, 2018 received in Canadian Patent Application No. 2,769,378.
Canadian Examination Report dated Feb. 22, 2017 received in Canadian Patent Application No. 2,769,378.
Chinese Office Action dated Apr. 15, 2014 received in Chinese Patent Application No. 201080042989.2, together with an English-language translation.
European Examination Report dated Apr. 10, 2019 received in European Patent Application No. 10 806 878.4.
Extended Supplementary European Search Report dated Oct. 24, 2017 received in European Patent Application No. 10 80 6878.4.
Japanese Decision of Rejection dated Jun. 4, 2019 received in Japanese Patent Application No. 2016-192628, together with an English-language translation.
Japanese Notice of Reasons for Rejection dated Mar. 19, 2019 received in Japanese Patent Application No. 2016-049343, together with an English-language translation.
Japanese Notice of Reasons for Rejection dated Feb. 7, 2017 received in Japanese Patent Application No. 2016-049343, together with an English-language translation.
English-language translation of Chinese Office Action dated Apr. 4, 2014 received in Chinese Patent Application No. 201080042989.2.
English-language translation of Chinese Search Report dated Apr. 4, 2014 received in Chinese Patent Application No. 201080042989.2.
International Search Report and Written Opinion dated Mar. 23, 2012 received from the Korean Intellectual Property Office in International Application No. PCT/US2011/045339.
International Search Report and Written Opinion dated Apr. 1, 2011 received from the Korean Intellectual Property Office in International Application No. PCT/US2010/043335.
International Preliminary Report on Patentability dated Jan. 31, 2012 received in International Application No. PCT/US2010/043335.
U.S. Office Action dated Oct. 31, 2018 received in U.S. Appl. No. 14/862,298.
U.S. Final Office Action dated Mar. 1, 2018 received in U.S. Appl. No. 14/862,298.
U.S. Office Action dated Oct. 24, 2017 received in U.S. Appl. No. 14/862,298.
U.S. Final Office Action dated Jun. 26, 2017 received in U.S. Appl. No. 14/862,298.
U.S. Office Action dated Feb. 16, 2017 received in U.S. Appl. No. 14/862,298.
U.S. Final Office Action dated Aug. 1, 2016 received in U.S. Appl. No. 14/862,298.
U.S. Office Action dated Dec. 1, 2015 received in U.S. Appl. No. 14/862,298.
U.S. Office Action dated Jun. 17, 2015 received in U.S. Appl. No. 12/844,345.
U.S. Final Office Action dated Jan. 22, 2015 received in U.S. Appl. No. 12/844,345.
U.S. Office Action dated Jul. 15, 2014 received in U.S. Appl. No. 12/844,345.
U.S. Final Office Action dated Nov. 8, 2013 received in U.S. Appl. No. 12/844,345.
U.S. Office Action dated May 3, 2013 received in U.S. Appl. No. 12/844,345.
Indian Examination Report dated Jan. 20, 2020 received in Indian Application No. 1648/CHENP/2012, together with an English-language translation.
Decision to Refuse dated Nov. 4, 2021 received in European Application No. 10 806 878.4.
Minutes of the Oral Proceedings dated Nov. 3, 2021 received in European Application No. 10 806 878.4.
Indian Examination Report dated Oct. 12, 2021 received in Indian Application No. 202048030886, together with an English-language translation.
Canadian Examination Report dated Oct. 13, 2021 received in Canadian Application No. 3,095,919.

* cited by examiner

ASSAY INFORMATION MANAGEMENT METHODS AND DEVICES

CROSS REFERENCE TO RELATED APPLICATIONS

This application is a continuation of U.S. patent application Ser. No. 14/862,298, filed Sep. 23, 2015, now U.S. Pat. No. 10,446,263, which is a divisional of U.S. patent application Ser. No. 12/844,345, filed Jul. 27, 2010, which claims the benefit of U.S. Provisional Application No. 61/271,873, filed Jul. 27, 2009, the entire contents of which are incorporated herein by reference.

FIELD OF THE INVENTION

The present teaching relates to methods, devices and systems for associating assay information with an assay consumable used in a biological assay.

BACKGROUND OF THE INVENTION

Numerous methods and systems have been developed for conducting assays. These methods and systems are essential in a variety of applications including medical diagnostics, veterinary testing, food and beverage testing, environmental monitoring, manufacturing quality control, drug discovery, and basic scientific research. During the manufacture and use of reagents and other consumables used in biological assays, the reagents and consumables are typically coded and labeled by the manufacturer in order to track them. In addition, a myriad of analytical parameters must be tracked in order to understand the analytical results of any given assay, often requiring input from various parallel tracking systems supplied by the manufacturer, user or both.

SUMMARY OF THE INVENTION

The present invention provides an assay system configured to use an assay consumable in the conduct of an assay, said assay system comprising a reader adapted to perform an operation selected from the group consisting of (i) reading information from an assay consumable identifier associated with said assay consumable; (ii) erasing information from said assay consumable identifier; (iii) writing information to said assay consumable identifier; and (vi) combinations thereof. In one embodiment, the information is used by said system to adjust one or more operations performed by said system before, during and/or after the conduct of an assay by said system.

In a specific embodiment, the information comprises information used to identify an element selected from the group consisting of (i) said assay consumable, (ii) one or more test sites within said consumable, (iii) a reagent and/or sample that has been or will be used in said consumable, and (iv) combinations thereof. For example, the information is used to distinguish a first test site within said consumable from a different test site within said consumable. In one embodiment, the information is consumable information selected from the group consisting of lot identification information; lot specific analysis parameters, manufacturing process information, raw materials information, expiration date; calibration data; threshold information; the location of individual assay reagents and/or samples within one or more test sites of the assay consumable; Material Safety Data Sheet (MSDS) information, and combinations thereof.

The information may also be sample information selected from the group consisting of the location of samples within said at least one test sites of the assay consumable; assay results obtained on said assay consumable for said sample; identity of samples that have been and/or will be assayed in said assay consumable; and combinations thereof. The information may include chain of custody information, e.g., information regarding the control, transfer and/or analysis of said sample. The chain of custody information may include information concerning the control, transfer and/or manufacture of said assay consumable, including but not limited to user identification; time and date stamp for said assay; location of said assay system during said assay; calibration and QC status of said assay system during said assay, custody and/or location information for said assay consumable before and after the conduct of said assay; assay results for said sample; and combinations thereof. Still further, the information is chain of custody information selected from the group consisting of time, date, manufacturing personnel or processing parameters for one or more steps during the manufacture of said assay consumable; custody, location and or storage conditions for said assay consumable following manufacture and/or betweens steps during the manufacture of said assay consumable; and combinations thereof.

In another embodiment, the information is consumable/test site information selected from the group consisting of consumable type and structure; location and identity of assay reagents included with said assay consumable; location and identity of assay reagents within an assay test site of said assay consumable; and combinations thereof.

Alternatively, the information is assay process information selected from the group consisting of assay parameters to be applied by said reader during the assay; a sequence of steps to be applied by said reader during said assay; the identity, concentration, and/or quantity of assay reagents to be used or added during said assay; the type or wavelength of light to be applied and/or measured by the reader during said assay; the temperature to be applied by the reader during said assay; an incubation time for said assay; statistical or analytical methods to be applied by the reader to raw data collected during said assay; and combinations thereof. In a further embodiment, the assay is a multi-step assay and said assay process information relates to a step or step(s) of said multi-step assay.

Still further, the consumable/test site information comprises information concerning assays previously performed by a reader on one or more test sites of said consumable; information concerning assays to be performed by an assay reader or a component thereof on one or more test sites within said consumable; and combinations thereof.

The information may further include consumable security information selected from the group consisting of information concerning assay consumable authentication; information concerning appropriate placement and/or orientation of said assay consumable in said system; information concerning defects in said assay consumable and/or a test site thereof; and combinations thereof.

The information may be used by said system to adjust the operation of a component of said assay system selected from the group consisting of one or more sensors; mechanisms to transport the assay consumables into and out of the system; mechanisms to align and orient the assay consumables with said one or more sensors and/or with electrical, mechanical or fluidic interfaces in said system; mechanisms, electronics or software to track and/or identify assay consumables; mechanisms to store, stack, move and/or distribute one or more consumables.

The invention further provides an assay system configured to use an assay consumable in the conduct of an assay comprising a reader adapted to perform an operation selected from the group consisting of (i) reading information from an assay consumable identifier associated with said assay consumable; (ii) erasing information from said assay consumable identifier; (iii) writing information to said assay consumable identifier; and (iv) combinations thereof; wherein said information comprises consumable/test site information selected from the group consisting of information concerning assays previously performed by a reader on one or more test sites of said consumable; information concerning assays to be performed by an assay reader or a component thereof on one or more test sites within said consumable; and combinations thereof.

The invention also provides an assay system configured to use an assay consumable in the conduct of an assay comprising a reader adapted to perform an operation selected from the group consisting of (i) reading information from an assay consumable identifier associated with said assay consumable; (ii) erasing information from said assay consumable identifier; (iii) writing information to said assay consumable identifier; and (iv) combinations thereof; wherein said information comprises consumable security information selected from the group consisting of information concerning assay consumable authentication; information concerning appropriate placement and/or orientation of said assay consumable in said system; information concerning defects in said assay consumable and/or a test site thereof; and combinations thereof.

Still further, the invention contemplates an assay system configured to use a multiplex enabled assay consumable in the conduct of a multiplexed assay, wherein said assay consumable comprises a plurality of test sites within which said multiplexed assay is performed and said assay system comprises a reader adapted to perform an operation selected from the group consisting of (i) reading information from an assay consumable identifier associated with said assay consumable; (ii) erasing information from said assay consumable identifier; (iii) writing information to said assay consumable identifier; and (iv) combinations thereof.

The invention also provides an assay consumable comprising an assay consumable identifier comprising information, wherein said assay consumable is selected from the group consisting of (i) an assay consumable comprising at least one assay test site for said assay; and (ii) a container adapted to hold one or more assay reagents.

In one embodiment, the invention provides a multiplex enabled assay consumable comprising (i) a plurality of test sites for an assay, wherein each of said test sites comprise a plurality of distinct assay domains, each of said domains comprising reagents for measuring a different analyte; and (ii) an assay consumable identifier comprising information used to identify an element selected from the group consisting of (i) said assay consumable, (ii) one or more test sites within said consumable, (iii) a reagent and/or sample that has been or will be used in said consumable, and (iv) combinations thereof.

The invention also contemplates a method of using an assay consumable in an assay system, wherein said assay consumable comprises a consumable identifier and said assay system comprises a reader adapted to perform an operation selected from the group consisting of (i) read information from said consumable identifier; (ii) erase information from said consumable identifier; (iii) write information to said consumable identifier; and (iv) combinations thereof; said method comprising the steps of (a) reading information from said consumable identifier; (b) conducting an assay in said assay system using said assay consumable; and (c) writing information resulting from said assay conducted in step (b) to said consumable identifier.

Still further, the invention provides a method of using an assay consumable in an assay system, wherein said assay consumable comprises a consumable identifier and said assay system comprises a reader adapted to perform an operation selected from the group consisting of (i) read information from said consumable identifier; (ii) erase information from said consumable identifier; (iii) write information to said consumable identifier; and (iv) combinations thereof, said method comprising the steps of (a) reading information from said consumable identifier; (b) conducting an assay in said assay system using said assay consumable; (c) writing information resulting from said assay conducted in step (b) to said consumable identifier; and (d) tracking use of said assay consumable.

In one embodiment, the invention provides a method of tracking use of an assay consumable comprising an assay consumable identifier and a plurality of test sites, said method comprising (a) reading test site usage information from said assay consumable identifier; (b) identifying, based on said test site usage information, an available test site on said consumable; (c) carrying out an assay using said available test site; and (d) writing updated test site usage information to said assay identifier.

Moreover, the invention provides a method of tracking the manufacture of an assay consumable, wherein said assay consumable comprises an identifier and one or more component parts and said manufacturing process includes one or more operations conducted by one or more manufacturing consumables each comprising a reader adapted to perform an operation selected from the group consisting of (i) reading manufacturing information from said identifier; (ii) erasing manufacturing information from said identifier; (iii) writing manufacturing information to said identifier; and (iv) combinations thereof; said method comprising (a) affixing said identifier to a first component of said consumable; (b) performing an operation of said manufacturing process; (c) writing manufacturing information to said identifier, wherein said manufacturing information comprises information related to the operation performed in step (b); (d) performing an additional step in said manufacturing process; and (e) writing manufacturing information to said identifier, wherein said manufacturing information comprises information related to the operation performed in step (d).

Also provided is an assay system configured to use an assay cartridge in the conduct of an assay, said assay system comprising a reader adapted to perform the following operations (i) reading cartridge lot identification information from a first consumable identifier associated with said assay consumable; (ii) reading lot specific parameters from an additional consumable identifier; (iii) using said lot identification information and said lot specific parameters to adjust one or more operations performed by said assay system before, during and/or after the conduct of an assay by said system. The lot specific parameters may be selected from the group consisting of (i) a revision level that determines schema used to interpret assay results and/or assay information; (ii) cartridge type; (iii) year of cartridge manufacture; (iv) cartridge lot number; (v) expiration date of cartridge and/or reagents used in said assay; (vi) a cross-talk correction matrix to account for chemical cross-reactivity; (vi) threshold values for assays to be conducted in said cartridge; (vii) a range for internal positive control(s) used in said assay; (viii) a ranges for each assay to be conducted in said cartridge for a positive control.

Still further, the invention provides an assay system configured to use a multi-well assay plate, an additional multi-well assay plate, and one or more sample tube racks in the conduct of an assay, said assay system comprising a reader adapted to perform the following operations (i) reading tube position information from a first consumable identifier associated with said one or more sample tube racks; (ii) reading assay information and lot specific parameters from an additional consumable identifier associated with said additional multi-well assay plate; (iii) using position information and said lot specific parameters to adjust one or more operations performed by said assay system before, during and/or after the conduct of an assay on said multi-well assay plate by said system; (iv) erasing information from said additional consumable identifier; and (v) writing information to said additional consumable identifier.

DETAILED DESCRIPTION OF VARIOUS EMBODIMENTS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The assay consumables and systems of the present invention include a variety of devices and configurations. In one embodiment, the assay system of the present invention includes an assay reader capable of conducting a biological assay using an assay consumable. The assay consumable comprises an identifier (referred to alternatively throughout the specification as an identifier, a consumable identifier, or an assay consumable identifier) and the assay system, reader or a component thereof comprises an identifier controller that interacts with the identifier. As described hereinbelow, the identifier includes information concerning the assay consumable, which may include but is not limited to, how the consumable is manufactured and handled prior to use and how the consumable is used in an assay system. Therefore, the assay system is configured to use an assay consumable in the conduct of an assay, and the assay system includes a reader adapted to perform an operation selected from (i) reading information from an assay consumable identifier associated with the assay consumable; (ii) erasing information from the assay consumable identifier; and/or (iii) writing information to the assay consumable identifier. The information may be used by the system to perform a variety of operations, e.g., to perform any aspect of a biological assay, tracking the use and/or performance of the assay consumable and/or the assay system, associating particular information unique to that assay consumable with that consumable so that the information may be accessed and used in subsequent applications in the same or a different assay system, and/or to adjust one or more operations performed by the system before, during and/or after the conduct of an assay by the system.

The assay systems contemplated by the present invention are used to conduct any type of diagnostic or analytical method known in the art. Such analytical methods include but are not limited to clinical chemistry assays (e.g., measurements of pH, ions, gases and metabolites), hematological measurements, nucleic acid amplification assays (e.g., polymerase chain reaction (PCR) and ligase chain reaction assays), immunoassays (e.g., direct, sandwich and/or competitive immunoassays and serological assays), oligonucleotide ligation assays, and nucleic acid hybridization assays. Any biological reagent that might be used in such analytical methods may be used in such systems, including but not limited to nucleic acids, nucleotides, oligonucleotides, DNA, RNA, PNA, primers, probes, antibodies or fragments thereof, antigens, small molecules, e.g., drugs or prodrugs, streptavidin, avidin, and biotin.

These systems may be portable, e.g., hand-held, and/or operated within a fixed laboratory or field setting, alone or in combination with one or more additional components, assay devices or systems. These systems may be used in a variety of applications, from field operations to laboratory settings, in a wide variety of industries, including but not limited to, medical, clinical, forensic, pharmaceutical, environmental, veterinary, biological, chemical, agricultural, waste management, hazardous chemical, drug testing, and in defense applications, e.g., for the detection of biological warfare agents. The assay systems and consumables used in the present invention may detect an analyte of interest by any suitable method, including but not limited to, optical, electromechanical, radiowave, electromagnetic, colorimetric, fluorimetric, chemiluminescent, electrochemiluminescent, radiochemical, nuclear magnetic resonance, enzymatic, fluorescent, particle-count, and cell-count based detection.

The assay consumable includes devices in which one or more steps of an assay process are conducted and such devices may include one or more test sites where an assay measurement is conducted. In one embodiment, the assay consumable includes at least one assay test site for an assay. A test site may include a plurality of distinct assay domains, at least two of the domains including reagents for measuring different analytes. Still further, the consumable may include a plurality of test sites for a plurality of individual assays. Alternatively, the assay consumable may be a component that provides a reagent or other assay component that is used by the system to conduct an assay. For example, the assay consumable may be a container with one or more compartments for holding assay reagents. The assay consumable (or test sites therein) may be single use or it may be reusable. The assay consumable may be configured to conduct one test or multiple tests (sequentially or in parallel).

Test sites, as used herein, refer to regions of a consumable that hold, contact and/or interrogate a sample. A test site may include a plurality of distinct assay domains, at least two such domains include reagents for measuring different analytes. Consumables may comprise multiple test sites which may hold, contact or otherwise interrogate distinct volumes (aliquots) of the same sample and/or volumes of different samples. A sector of an assay consumable refers to grouping of two or more test sites of the consumable. Each test site may be used to conduct a single measurement or multiple measurements on a volume of sample (for example, the measurement of multiple different analytes in a multiplexed assay format). Depending on the specific requirements of an application, a consumable with multiple test sites may be configured to use all of its test sites in parallel, to use its test sites at different times (e.g., assigning unused test sites to be used as new samples are delivered to the assay system), or a combination of both modes of operation may be enabled.

The assay consumable may be any structure useful in diagnostic applications and that structure may be dictated by the particular assay format or detection method employed by the device. Examples of assay consumables suitable for use with the invention include, but are not limited to, test tubes, cuvettes, flow cells, assay cartridges and cassettes (which may include integrated fluidics for assay processing), multi-well plates, slides, assay chips, lateral flow devices (e.g., strip tests), flow-through devices (e.g., dot blots), pipette tips, solid phase supports for biological reagents and the like. In certain embodiments, test sites in the assay consumable are defined by compartments in the assay consumable, e.g., wells, chambers, channels, flow cells and the like. The assay consumable and/or test sites may include one or more components used to carry out an assay measurement according to one or more specific detection methodologies. Depending on the function of the consumable and the detection modalities employed by the assays system, examples of such components may include, but are not limited to, lateral flow matrices, filtration matrices, optical windows, sensors (e.g., electrochemical and optical sensors), solid phase supports for binding reactions (e.g., coated slides, chips, beads, pins, coated filtration or lateral flow matrices, tubes and the like), reagents (dry or in liquid form), electrodes, analyte selective membranes and the like.

In one embodiment, the assay consumable may be a device that incorporates a conventional lateral flow test strip, e.g., an immunoassay test strip, as an assay medium. In this example, the device is molded to include an identifier or the identifier is affixed to the device without any modification to the structure of the device and/or the assay medium. In one embodiment, the device is placed within the analytical system, i.e., the assay system, for analysis and before, during or after the performance of the assay, the identifier controller within, affixed to or associated with the assay system reads the data contained on the identifier and uses that data in the assay or after the assay is completed by the system.

In another embodiment, the assay consumable and accompanying assay system or reader is capable of performing a multiplex assay. A multiplex assay is a type of assay in which multiple measurements are performed on a single sample, e.g., by distributing samples across multiple test sites and/or by carrying out multiple measurements on volumes of samples in individual test sites. The multiple measurements may include, but are not limited to, (i) multiple replicates of a measurement for an analyte; (ii) multiple measurements of a certain analyte (i.e., multiple non-identical measurements for the same analyte, e.g., measurements that differ in format or in the identity of the assay reagents that are employed); and/or (iii) measurements of multiple different analytes. In one specific embodiment, an assay consumable is configured to carry out, in one or more test sites, multiplex measurements that include at least two assays for two different analytes.

The invention is not restricted to specific approaches for conducting multiplex measurements in a test site and may employ any of the numerous techniques that have been developed for carrying out multiplex measurements. Multiplex measurements that can be used with the invention include, but are not limited to, multiplex measurements (i) that involve the use of multiple sensors; (ii) that use discrete assay domains on a surface (e.g., an array) that are distinguishable based on location on the surface; (iii) that involve the use of reagents coated on particles that are distinguishable based on a particle property, such as size, shape, color, etc.; (iv) that produce assay signals that are distinguishable based on optical properties (e.g., absorbance or emission spectrum), (v) that are based on temporal properties of an assay signal (e.g., time, frequency or phase of a signal), and/or (vi) that are based on some other assay characteristic. Accordingly, interpretation of multiplexed assay results may involve the use of multiplexing information, such as the identity of the assays carried out in each test site and, within a test site, any assay characteristics (identity of specific sensors, location and identity of assay domains, etc.) that are used to distinguish assays carried out in a test site and/or that are used to tie a specific assay identity to the corresponding assay signal.

In one embodiment, an assay test site comprises a plurality of distinct assay domains and each domain comprises one or more reagents for measuring a different analyte. Multiplexing information, including the location, identity, and composition of each assay domain, is used to identify the assay signal generated at each domain and connect it to a determination of the presence or amount of the corresponding analyte (a process which may include the application of additional assay information such as signal thresholds and/or calibration parameters).

A test site may be configured to carry out a plurality of multiplexed measurements (e.g., it may include a plurality of distinct assay domains, wherein each domain comprises reagents for measuring a different analyte). In one embodiment, the assay consumable may include a plurality of test sites. Information regarding the exact configuration of the one or more test sites, assay domains, and/or one or more sectors in a consumable may be included in the information saved to the assay consumable identifier. This information may include the location and identity of the test sites, assay domains, and/or one or more sectors as well as multiplexing information (as described above) including the number, identity and differentiating characteristics of the individual measurements within a test site, assay domain, and/or sector (e.g., the specific locations, identities and/or assay reagents of assay domains within each test site). In addition, the use of a test site, assay domain, and/or sector in an assay consumable may also be recorded to the identifier to track the use of the consumable in an assay system. The identifier may also include information concerning the assay format and specific processing steps to be used for an assay consumable or test site, assay domain, and/or sector of an assay consumable. The identifier may also include information concerning analytical methods that should be applied by the system once an assay is conducted to analyze the output of an assay in a given test site, assay domain, and/or sector and, optionally, to provide results that combine the output from multiple assays in a test site, assay domain, and/or sectors.

The test sites may be configured in any suitable configuration, depending on the geometry of the consumable and/or the type of assay conducted with the consumable. In one embodiment, the test sites are configured as wells and/or chambers in the assay consumable. For example, the assay consumable of the present invention may be a multi-well plate (e.g., a 24-, 96-, 384- or 1536-well plate), and the wells of the plate can further comprise a plurality (e.g., 2 or more, 4 or more, 7 or more, 25 or more, 64 or more, 100 or more, etc.) of distinct assay domains. Multi-domain multi-well plates that are adapted to allow assay measurements to be conducted using electrode induced luminescence measurements (e.g., electrochemiluminescence measurements) are described in U.S. application Ser. No. 10/238,391, entitled "Methods and Reader for Conducting Multiple Measurements on a Sample", filed on Sep. 10, 2002, hereby incorporated by reference. The exact configuration of the domains, test sites, and/or sectors in an assay consumable, as well as the specific identity of each domain, test site, and/or sector and the reagents bound to that domain/test site/sector may be included in the information saved to the assay consumable identifier. In addition, the use of a given domain, test site, and/or sector in an assay consumable may also be recorded to the identifier to track the use of the consumable in an assay system.

Assay consumables can be used in a plurality of diverse assays and this diversity leads to a variety of suitable configurations of the associated consumable. In one assay format, the same analyte is measured at different assay domains within a test site, the different assay domains being designed to measure a different property or activity of the analyte. Information concerning the assay format that may be used in an assay consumable, test site and/or assay domain may also be saved to the assay consumable identifier. The identifier may also include information concerning analytical methods that should be applied by the system once an assay is conducted to analyze the output of an assay in a given test site and/or domain and compare that output to an assay in a separate test site and/or domain.

One example of a multiplex assay consumable and reader is described in U.S. 2004/0022677, the disclosure of which is incorporated herein by reference in its entirety. Such assay consumables include one or more, and in one embodiment, a plurality of test sites and/or assay domains for conducting one or more assay measurements simultaneously or sequentially. For example, the test sites may be configured as wells and/or chambers. These test sites and/or assay domains comprise one or more electrodes for inducing luminescence from materials in the test sites and/or assay domains. The assay consumables may further comprise assay reagents in liquid or dry form, e.g., in the test sites, e.g., wells or chambers, of the consumable.

In addition to the test sites and assay domains, an assay consumable or multi-well assay plate may include several additional elements, e.g., a plate top, plate bottom, wells, working electrodes, counter electrodes, reference electrodes, dielectric materials, electrical connections, and assay reagents. The wells of the plate may be defined by holes or openings in the plate top, or as indentations or dimples on a surface of a plate. The plates may have any number of wells of any size or shape, arranged in any pattern or configuration and can be composed of a variety of different materials. Exemplary embodiments of consumables that may be used in the present invention include industry standard formats for the number, size, shape and configuration of the plate and wells, e.g., 96-, 384-, and 1536-well plates, with the wells configured in two-dimensional arrays. Other formats may include single well plates, 2-well plates, 6-well plates, 24-well plates, and 6144-well plates. Multi-well assay plates may be used once or may be used multiple times and are well suited to applications where the plates are disposable. Various configurations for suitable assay plates may be used in the present invention, including but not limited to those depicted in FIGS. 11A, 12A, 13A, 13B, 14A, 15, and 16A of U.S. Application Ser. No. 2004/0022677, each of which are incorporated herein by reference. As stated above, the specific configuration and identity of assay test sites, domains, and/or sectors of an assay consumable may be included in the information saved to the assay consumable identifier.

In this embodiment, the assay consumables may be used in a reader that can be used to induce and measure luminescence, e.g., electrode induced luminescence or electrochemiluminescence, in assays conducted in or on assay consumables, e.g., multi-well assay plates. The accompanying assay system can also induce and/or measure current and/or voltage, for example, at an electrode. The assay system may incorporate, for example, one or more photodetectors; a light tight enclosure; mechanisms to transport the assay plates into and out of the reader (and in particular, into and out of a light tight enclosure); mechanisms to align and orient the assay plates with the photodetector(s) and/or with electrical contacts; additional mechanisms to track and identify plates (e.g. bar code readers); mechanisms to make electrical connections to plates, one or more sources of electrical energy for inducing luminescence, and appropriate devices, electronics and/or software. The assay reader may also include mechanisms to store, stack, move and/or distribute one or more multi-well assay plates (e.g. plate stackers and/or plate conveyors) The assay system may be configured to measure light from multi-well assay plates by measuring light sequentially from a plurality of sectors or regions of the plate (i.e., a grouping of a plurality of adjacent assay domains within a plate) and/or from the entire plate substantially simultaneously or simultaneously. The assay system may also incorporate additional microprocessors and computers to control certain functions within the system and to aid in the storage, analysis and presentation of data. Various configurations for suitable assay systems may be used in the present invention, including but not limited to those depicted in FIGS. 17 to 23 of U.S. Application Ser. No. 2004/0022677, each of which are incorporated herein by reference.

The additional microprocessors and computers in the assay system may also interact with the assay consumable identifier microprocessor or controllers by transferring data and commands to/from the identifier to the various microprocessors/controllers throughout the system to perform various operations of the components listed above within the assay system.

One assay procedure using an assay consumable, e.g., a multi-domain multi-well plate, and an assay system would comprise inserting the consumable in the system to allow the identifier controller to interact with the identifier affixed to or associated with the consumable. Alternatively, the consumable packaging includes the identifier affixed thereto or associated therewith and before the consumable is inserted into the system, the identifier associated with the consumable packaging is contacted with the identifier controller. The system may adjust the assay parameters prior to initiating an assay based on the assay information saved to the identifier. Thereafter, the system makes the appropriate electrical, fluidic and/or optical connections to the consumable (making use of electrical, fluidic and/or optical connectors on the consumable and system) and conducts an assay using the consumable. The sample may be introduced into the consumable prior to inserting the consumable in the system. Alternatively, the sample is introduced by a component of the system after the consumable is inserted in the system. The assay may also involve adding one or more assay reagents to the consumable and instructions for adding those various assay reagents may be saved to the identifier and the system adds those reagents to the consumable before or during the assay according to the instructions saved to the assay consumable identifier.

Alternatively, the assay consumable is a cartridge and the consumable further comprises an element selected from one or more fluidic components, one or more detection components, one or more assay cells, reagents for carrying out an assay, working electrodes, counter electrodes, reference electrodes, dielectric materials, electrical connections, dried and/or liquid assay reagents, and combinations thereof. The cartridge may further comprise at least one assay cell that comprises a plurality of distinct assay test sites and/or domains, each of these test sites and/or domains comprising reagents for measuring a different analyte.

An example of an assay consumable cartridge that may be used in the present invention is described in US Application Ser. No. 2004/0189311, the disclosure of which is incorporated herein by reference in its entirety. The assay consumable described therein is an assay cartridge that incorporates one or more fluidic components such as compartments, wells, chambers, fluidic conduits, fluid ports/vents, valves, and the like and/or one or more detection components such as electrodes, electrode contacts, sensors (e.g. electrochemical sensors, fluid sensors, mass sensors, optical sensors, capacitive sensors, impedance sensors, optical waveguides, etc.), detection windows (e.g. windows configured to allow optical measurements on samples in the cartridge such as measurements of absorbance, light scattering, light refraction, light reflection, fluorescence, phosphorescence, chemiluminescence, electrochemiluminescence, etc.), and the like. Such consumables may also comprise reagents for carrying out an assay such as binding reagents, detectable labels, sample processing reagents, wash solutions, buffers, etc. The reagents may be present in liquid form, solid form and/or immobilized on the surface of solid phase supports present in the cartridge. In this embodiment, the consumables include all the components necessary for carrying out an assay. In addition, the assay consumable is used in connection with a consumable reader adapted to receive the consumable and carry out certain operations on the consumable such as controlling fluid movement, supplying power, conducting physical measurements on the cartridge, and the like.

More specifically, such assay consumable cartridges have one or more assay test sites (e.g., wells, compartments, chambers, conduits, flow cells, etc.) that may include one or more assay domains (e.g., discrete locations on a assay test site surface where an assay reaction occurs and/or where an assay dependent signal, such as an electrochemical or an electrode induced luminescence signal is induced) for carrying out a plurality of assay measurements. In this embodiment, assay domains are supported on assay electrodes (in one embodiment, an array of assay electrodes, e.g., a one dimensional array of assay electrodes) so as to permit the conduct of assays based on electrochemical or electrode induced luminescence measurements. The assay domains are, optionally, defined by a dielectric layer deposited on the electrodes. In addition, the assay consumables may have one or more attributes that make them suitable for use in "point of care" clinical measurements, e.g., small size, low cost, disposability, multiplexed detection, ease of use, etc.

The assay consumable cartridge may comprise the necessary electronic components and/or active mechanical components for carrying out an assay measurement, e.g., one or more sources of electrical energy, ammeters, potentiometers, light detectors, temperature monitors or controllers, pumps, valves, etc. Alternatively, some or all of the electronic and/or active mechanical components are arranged within a separate assay reader. The reader would also have the appropriate electrical, fluidic and/or optical connections to the assay consumable for carrying out an assay using the consumable. Using such an arrangement, the assay consumable can be designed to be low cost and disposable while the reader (which holds the more expensive and complex components) reusable.

An assay procedure using an assay consumable cartridge and an assay system, e.g., an assay reader, may include inserting the cartridge in the reader to allow the identifier controller to interact with the identifier affixed to or associated with the cartridge. Alternatively, the cartridge packaging includes the identifier affixed thereto or associated therewith and before the cartridge is inserted into the reader, the identifier of the cartridge packaging is contacted with the identifier controller. The reader may adjust the assay parameters prior to initiating an assay based on the assay information saved to the identifier. Thereafter, the reader makes the appropriate electrical, fluidic and/or optical connections to the cartridge (making use of electrical, fluidic and/or optical connectors on the cartridge and reader) and conducts an assay in the cartridge. The sample is may be introduced into the cartridge prior to inserting the cartridge in the reader. The assay may also involve adding one or more assay reagents to the cartridge and instructions for adding those various assay reagents may be saved to the identifier and the reader adds those reagents to the cartridge before or during the assay according to the instructions saved to the assay consumable identifier.

In one embodiment, a cartridge-based biochemical detection system may include a system housing comprising an optical detector wherein the system housing is adapted and configured to receive and position the assay consumable and/or the optical detector for processing. The system may further comprise support subsystems that may include one or more of the following: storage subsystem for storing assay reagents/consumables and/or waste; sample acquisition/preprocessing/storage subsystem for sample handling; fluidic handling subsystem for handling the reagents, sample, waste, etc. and for providing fluids to the detection chamber via a fluid inlet line; electrical subsystem for electrically contacting the cartridge's electrical contacts and supplying electrical energy to the electrodes; and a control subsystem for controlling and coordinating operation of the system and subsystems and for acquiring, processing and storing the optical detection signal. The information stored to the assay consumable identifier may include information that is used to control or adjust one or more of the assay system components prior to and/or during the conduct of an assay using the assay consumable.

Still further, the assay consumable may be a container holding one or more assay reagents, including but not limited to one or more buffers, diluents, and/or reagents used by the assay system in the conduct of an assay. The assay consumable identifier may be affixed to the container and/or affixed to a packaging for the container.

In one embodiment, the assay consumable identifier comprises memory for storing information related to the consumable, its history and/or its use. In one embodiment, the memory is non-volatile memory. Non-volatile memory is computer memory that can retain the stored information without power. Examples of non-volatile memory which may be used in the consumable identifier include, but are not limited to, electronic non-volatile memory (e.g., read-only memory and flash memory), magnetic memory (e.g., hard disks, floppy disk drives, and magnetic tape), optical memory (optical disc drives) and hybrids of these approaches (e.g., magneto-optical memory).

In one embodiment, the assay consumable identifier comprises EPROM (erasable programmable read-only memory), a type of programmable read-only memory that can be erased by exposing it to ultraviolet light. Once erased, it can be reprogrammed with new or modified data. In another embodiment, the assay consumable identifier comprises EEPROM (electronically erasable programmable read-only memory) a class of non-volatile electronic memory that can be electrically erased and reprogrammed without exposure to UV light. An EEPROM can be written to or programmed more than once and can be selectively programmed (the user can alter the value of certain cells without erasing the programming of the other cells). Therefore, sections of data can be erased and replaced without needing to alter or reinstall the rest of the chip's programming.

In another embodiment, the assay consumable identifier comprises flash memory, a specific type of EEPROM that is erased and programmed in large blocks. Although flash memory is technically a type of EEPROM, the term "EEPROM" is generally used to refer specifically to non-flash EEPROM which is erasable in small blocks, typically bytes. Because erase cycles are slow, the large block sizes used in flash memory erasing give it a significant speed advantage over conventional EEPROM when writing large amounts of data.

In another embodiment, the assay consumable identifier comprises a smart card, chip card, or integrated circuit card (ICC) (referred to collectively as "ICCs"). These are small cards with embedded integrated circuits which can process and store data. There are two broad categories of ICCs; i) "memory cards" that contain non-volatile memory storage components and, optionally, some specific security logic but do not contain microprocessors and ii) "microprocessor cards" that combine non-volatile memory components with microprocessor components and enable the processing of information being read into or out of the ICC. The ICC electronic components are supported on a card that is, typically, made of plastic such as PVC or ABS. The card may include an embedded hologram to avoid counterfeiting. Contact ICCs have conductive contact pads. When inserted into a reader, the contact pads on the ICC make contact with electrical connectors in the reader to allow for transfer of information between the reader and the ICC, for example, allowing the reader to read, erase or write information on the ICC.

Another method of transferring information is via an RFID, i.e., radio frequency identification, which is similar in theory to bar code identification. With RFID, the electromagnetic or electrostatic coupling in the RF portion of the electromagnetic spectrum is used to transmit signals. An RFID system consists of an antenna and a transceiver, which read the radio frequency and transfers the information to a processing device, and a transponder, or tag, which is an integrated circuit containing the RF circuitry and information to be transmitted.

Identification can also be accomplished by reading a bar code. One of the key differences between RFID and bar code technology is that RFID) eliminates the need for line-of-sight reading that bar coding depends on. Also, RFID scanning can be done at greater distances than bar code scanning. High frequency RFD systems (850 MHz to 950 MHz and 2.4 GHz to 2.5 GHz) offer transmission ranges of more than 90 feet, although wavelengths in the 2.4 GHz range are absorbed by water (the human body) and therefore has limitations.

In one embodiment, the non-volatile memory used in the present invention is selected from the group consisting of an EEPROM, flash memory, ICC and combinations thereof. In one embodiment, the non-volatile memory is an EEPROM. In an alternate embodiment, the non-volatile memory is an RFID.

In an additional alternative embodiment, two or more non-volatile memory components may be used in the present invention. For example, a first assay consumable comprising a first identifier may be used in the assay system, and an additional assay consumable comprising an additional identifier may also be used in the assay system. Each identifier may include the same or different type of memory. However, for each different form of memory, there will be a separate identifier controller. And certain assay information may be stored on one identifier and other assay information on an additional identifier of the same or different type. For example, one assay consumable used in the system may comprise an EEPROM or RFID as an identifier, whereas the system may also use an additional assay consumable comprising, e.g., a bar code as a identifier. The assay system would comprise an identifier controller capable of interfacing with the first identifier, i.e., the EEPROM or RFID, and the system will further comprise an additional controller that will interface with the bar code.

The assay system of the present invention includes an identifier controller that controls the operation of the non-volatile memory and other components of the assay system. The identifier controller optionally includes a micro-controller to interface with the non-volatile memory over a communication interface, which may incorporate conventional interface architectures and protocols such as $I^2C$, a two line serial bus protocol. The microcontroller addresses the non-volatile memory and performs write, read and erase operations on the memory.

The consumable identifier may be located on the consumable or it may be a separate component. In either case, the system may be designed to have a unique identifier for each consumable. Alternatively, the system may be configured so that one separate consumable identifier is used to hold information relating to a plurality of consumables. In one example, each package of consumables has a package-specific identifier mounted on the package (or, alternatively, supplied in the package) that holds information relating to the plurality of consumables in the package. Optionally, each consumable also carries an additional unique consumable-specific identifier attached to the consumable. This consumable-specific identifier is used primarily to uniquely identify the consumable and link it to information on the package-specific identifier. In this embodiment, lot information content and/or non-editable identifiers such as bar codes may be used.

The various components of the assay system may be housed together in a single unit or may be housed separately. For example, the assay system may include an assay reader and an identifier controller as separate units. The assay system provides for communication (which may be wired or wireless communication) directly between the assay reader and identifier controller or, alternately, indirectly through additional components of the assay system. In an alternative embodiment, the identifier controller is housed within the assay reader. In such an embodiment, the assay reader may be configured such that insertion of the consumable into the reader during the conduct of an assay also enables communication between the consumable identifier and the identifier controller (e.g., a port into which the consumable is inserted includes components for processing and/or reading the consumable and also includes components, such as electrical contacts or a radio transmitter, for communicating with the consumable identifier). In one example, when the consumable is loaded into the assay system, electrical contacts are made between the controller and the identifier, e.g., non-volatile memory. The controller is then able to read, erase and/or write assay information to the identifier. Alternatively, the assay reader may have separate ports for processing/reading a cartridge and for communicating with the consumable identifier. The user places the assay consumable or packaging in or in proximity to the controller port such that the controller makes electrical contact with the identifier to enable the controller to read, erase and/or write assay information to the non-volatile memory In one embodiment, the identifier comprises non-volatile memory selected from the group consisting of an RFID tag, a bar code, an EPROM, and EEPROM. Still further, the identifier may comprise an EEPROM selected from the group consisting of flash memory and ICC.

The identifier is programmed, e.g., during the manufacturing process or at another time prior to use in the assay system. The identifier may be programmed with information (referred to herein as "assay information") which is used before, during or after an assay or a step of a multi-step assay to control the operation of the assay system, reader or a component of the assay system. The term "assay information" may include any information used to uniquely identify a particular assay or assay step, assay consumable, consumable domain(s), biological reagent or sample or to distinguish a particular assay, assay step, assay consumable, consumable domain(s), biological reagent or sample from other assay consumables, consumable domains, biological reagents or samples. Assay information may include consumable information, sample information, chain of custody information, consumable/test site information, assay process information, consumable security information, and combinations thereof. Each type of assay information is described in more detail below.

For example, the assay information may include consumable information that includes but is not limited to lot identification information, lot specific analysis parameters, manufacturing process information, raw materials information, expiration date, Material Safety Data Sheet (MSDS) information, product insert information (i.e., any information that might be included or described in a product insert that would accompany the assay consumable, e.g., the assay type, how the assay is performed, directions for use of the assay consumable, assay reagents, or both, etc.), threshold and/or calibration data for one or more reagents used in the assay consumable or in an assay or a step of a multi-step assay, and the location of individual assay reagents and/or samples within one or more test sites of the assay consumable.

The consumable identifier may also include lot identification information, i.e., information that is used to identify a particular lot of assay consumables, which is distinct from lot-specific analysis parameters, which includes that information that is unique to a given lot that may be used by the system, e.g., to conduct an assay with a consumable from that lot or to analyze assay results derived from a consumable from that lot. In one embodiment, if the assay consumable is a multi-well assay plate or a cartridge, the lot-specific analysis parameters may include, but are not limited to, the following: (i) the revision level that determines the schema used to interpret the information; (ii) the consumable type; (iii) the date of manufacture; (iv) the lot number; (v) the date of expiration; (vi) a cross-talk correction matrix, to account for chemical cross-reactivity; (vii) a threshold for assays to be conducted in the consumable and each internal negative control; (viii) a range for each internal positive control; (ix) ranges for each assay to be conducted in the cartridge for the positive control sample; (x) a software checksum to ensure integrity of the data; (xi) in-well (or in-test site) control acceptance ranges; (xii) assay names and/or identifiers; (xiii) information concerning assay quality control, including negative and positive quality control materials that are used to verify the operation of the reader and the consumable; (xiv) calibration information such as a master calibration curve; and (xv) number and names of assay calibrators and/or assay calibrator acceptance ranges.

The assay information may include sample information, such as the location of samples within at least one test site of the assay consumable, assay results obtained on said assay consumable for the sample, and the identify of samples that have been and/or will be assay in the assay consumable.

The assay information may also relate to chain of custody, e.g., information regarding the control, transfer and/or analysis of the sample and/or an assay consumable. Chain of custody information may be selected from user identification, sample identification, time and date stamp for an assay, the location of the assay system in a laboratory during the assay, calibration and QC (quality control) status of the assay system during the assay, custody and/or location information for the assay consumable before and after the conduct of the assay, assay results for a given sample, as well as user created free text comments input before, during or after an assay is processed by the system. Still further, chain of custody information may include time, date, manufacturing personnel or processing parameters for one or more steps during the manufacture of the assay consumable, custody, location and/or storage conditions for the assay consumable following manufacture and/or between steps during the manufacture of the assay consumable.

Assay information may also include consumable/test site information, such as consumable type and structure, the location and identity (e.g., the structure, composition, sequence, concentration and/or origin) of assay reagents included within an assay consumable, and the location and identity of assay reagents within an assay test site of the assay consumable.

In addition, the assay information may include assay process information concerning the individual assay parameters that should be applied by the system or reader during the assay. For example, such assay information may include a sequence of steps for a given assay, the identity, concentration and/or quantity of assay reagents that should be used or added during the assay or during a particular step of an assay, e.g., buffers, diluents, and/or calibrators that should be used in that assay. In addition, the assay information may include data regarding how one or more steps in an assay protocol (e.g., dilution or reagent addition steps) may be adjusted to account for lot to lot or consumable to consumable differences. The amount of diluent added and/or the nature of the diluent may be altered based on such differences. Similarly, the amount of a given reagent that may be added during the conduct of an assay, an incubation period and/or temperature for one or more steps of an assay may also be dependent on lot to lot or consumable to consumable differences.

The assay information may also include the type or wavelength of light that should be applied and/or measured by the system or reader during the assay or a particular step of a multi-step assay; the temperature that should be applied by the system or reader during the assay; the incubation time for an assay; and statistical or other analytical methods that should be applied by the system or reader to the raw data collected during the assay.

In an additional embodiment, the information includes consumable/test site information i.e., information concerning assays previously performed by a reader on one or more test sites of the consumable, and information concerning assays to be performed by a reader on one or more test sites within the consumable. Therefore, once the assay is conducted by the system, the controller may be used to write the results of the assay to the identifier. Such information includes, but is not limited to raw or analyzed data collected by the system during the assay (wherein analyzed data is data that has been subjected to statistical analysis after collection and raw data is data that has not been subjected to such statistical analysis), a list of test sites and/or domains within the assay consumable used during a given assay, a schedule of events to be conducted on an assay consumable or a test site and/or domain within an assay consumable, a list of those test sites and/or domains of the assay device that have not be subjected to an assay, assay or system errors that resulted during a given assay or assay step, and combinations thereof.

Moreover, the information comprises data that directly or indirectly controls a component of the assay system, e.g., one or more photodetectors, a light tight enclosure; mechanisms to transport the assay consumables into and out of the reader; mechanisms to align and orient the assay consumables with the one or more photodetector(s) and/or with electrical contacts in the reader; additional mechanisms and/or data storage media to track and/or identify assay consumables; one or more sources of electrical energy to induce luminescence; mechanisms to store, stack, move and/or distribute one or more consumables; mechanisms to measure light from a consumable during the assay sequentially, substantially simultaneously or simultaneously from a plurality of test sites of the consumable; and combinations thereof.

Still further, the identifier/controller in the assay system may be used as a security mechanism, e.g., to confirm that the correct assay consumable is being used in the system (referred to herein as "consumable security information"). The assay information may include a digital signature to prove that the consumable was manufactured by the designated vendor. In one embodiment, if an inappropriate assay consumable is present in the system, e.g., a counterfeit consumable or a consumable that is otherwise incompatible with the assay system, the controller will disable the system, reader or a component thereof. In addition or alternatively, the identifier/controller may be used to detect the proper placement of the assay consumable in the system, e.g., the proper orientation of the assay consumable or a portion thereof, in the assay system, such that the controller will disable the system, reader or a component thereof until the assay consumable is placed in the correct orientation. Still further, the identifier/controller in the system may also be used to detect a defect in the assay consumable or an assay test site and/or domain and the controller will disable the system, reader or a component thereof accordingly. For example, depending on the nature of the defect in the assay consumable or domain, the controller may disallow the use of the assay consumable in its entirety or direct the reader to disallow the use of a test site and/or domain or a set of test site and/or domain in the assay consumable. In one embodiment, the reader may perform a diagnostic analysis on the assay consumable and/or a test site and/or domain therein to identify defects therein and the controller will write the results of that diagnostic analysis to the identifier on the consumable. If the consumable is later used in a different reader, the results of this diagnostic analysis will be read by the controller and used by the reader to adjust the use of that consumable or a test site and/or domain in that consumable accordingly. In a further embodiment, the assay consumable may be subjected to a quality control process during or after its manufacture and the results of that quality control analysis may be written to the identifier for later use and/or verification by the user of the assay consumable in an assay reader.

The assay information may also include authorization information for consumables or test site and/or domain thereof or biological reagents, such as information regarding whether a particular user has a valid license to use a particular consumable or biological reagent, including the number of times the user is permitted to use the particular consumable or biological reagent in a particular assay and the limitations, if any, on that use, e.g., whether the user's license is for research purposes only. Such information can also include validation information regarding whether a particular consumable or biological reagent has been subject to a recall or has otherwise become unsuitable or unauthorized for use. The recall information and an optional last recall check date and/or timestamp can be written to the identifier.

The assay information may further include information regarding the origin of a biological reagent used in an assay consumable, test site and/or domain, including for example an identification of an original sample from which it was derived or the number of generations removed it is from an original sample. For example, if an assay reagent used in an assay is an antibody, the assay information may include the identification of the hybridoma from which the antibody was derived, e.g., the ATCC accession number for that hybridoma.

The assay information may additionally include information regarding a consumable, test site, domain, sector, or a biological reagent or sample as individual operations are performed on that consumable, test site, domain, sector, or biological reagent or sample, for example during manufacture of the consumable, test site, domain, sector, or biological reagent or while an assay or step is being performed on the consumable, test site, domain, sector, or biological reagent or sample. For example, if an assay consumable includes a plurality of assay test sites, domains, and/or sectors, the assay system may perform an assay or step of a multi-step assay on a single test site, domain and/or sector of the assay consumable. Once that assay or assay step is completed by the assay system, the controller records the results of that assay, e.g., the raw or analyzed data generated during the assay or assay step, to the identifier, and/or the controller records which test site, domain and/or sector of the assay consumable were used during the assay or assay step and/or which test site, domain and/or sector of the assay consumable have yet to be used. The assay consumable may be stored for later use and when the user is ready to use another test site, domain and/or sector of the assay consumable, the controller reads the assay information stored on the identifier of the assay consumable to identify which test site, domain and/or sector has been used, has yet to be used, and/or the results of those assays. The controller may then instruct the assay system, reader or component thereof to conduct an assay or assay step on an unused test site, domain and/or sector.

In addition, a given assay protocol may require a set of consumables of a particular type. Therefore, if the user inputs a specific type of assay consumable, e.g., a multi-well assay plate, for use in a particular assay protocol, one or more additional assay consumables may be required to carry out that assay protocol in the system, e.g., one or more reagents may be required for use with that multi-well assay plate. Each of the required consumables may include a consumable identifier with information concerning the consumable requirements for an assay protocol. When one of the required consumables is input into the assay system and the identifier controller interacts with the consumable identifier for that consumable, the system will take an inventory of the components present in the system and compare the results to the consumable requirements stored to the consumable identifier. If any required consumables are not present or are present in insufficient supply, the system will prompt the user to input the additional required consumables for that assay protocol based on the information stored on the required consumable identifier. If two or more assay consumables are used in the system, the instrument will correctly identify a first assay consumable and any associated consumables based on the consumable requirements stored to the identifiers associated with each consumable. The system will verify that the assay consumable and associated consumables are loaded on the system before the sample is run. In the case where only the first assay consumable is loaded into the system without the corresponding associated consumable, the system will prompt the user to load the associated consumable if the instrument does not identify the associated consumable within the system within a predefined period of time. The system will notify the user if mismatched assay consumables are loaded on the instrument. The system will not run samples if there are no available matched sets of assay consumables (e.g., multi-well assay plates and given reagents for a particular assay). The system will check for assay consumable expiration prior to the start of an assay and the system will alert the user and prevent the use of an expired consumable. The system will not process a sample if the consumables have expired prior to sample aspiration. If a partially used assay consumable is installed into a different instrument, consumable usage will automatically start with the next available unused well.

The identifier may also be used to track the time a given assay consumable is present in the assay system. Therefore, when an assay consumable is inserted into or contacted with an assay system, a timer is initiated in the assay system and the start time is recorded to the identifier. When the assay is initiated by the system on the consumable or a test site, domain and/or sector within the consumable, the time is also recorded to the identifier. If the instrument, system or a component thereof is shutdown by turning the power off), the timer is stopped and that time is recorded to the identifier. Thus, whenever the timer is stopped, the accumulated onboard time is recorded to the identifier.

According to various embodiments, biological samples or reagents that are provided in the carriers described above are licensed separately from systems designed to operate on the biological reagents. In various embodiments the assay system, reader or a component thereof is coupled to a network that allows the system to communicate over public and/or private networks with computer systems that are operated by or on behalf of the users, manufacturers and/or licensors of the biological reagents, consumables or systems. In various embodiments, a limited license can provide for the use of licensed biological reagents, consumables or systems for a particular biological analysis on only licensed systems. Accordingly, a system can authenticate a biological reagent, consumable or system based on, for example, a digital signature contained in the identifier associated with a particular consumable, if a particular user has a valid license. In various embodiments, the identifier can also be programmed to provide for a one time use such that biological reagents cannot be refilled for use with the same authentication.

In certain embodiments, when the identifier is read by a system, reader or component thereof that has access to a public or private data network operated by or on behalf of the users, manufacturers and/or licensors of the biological reagents, consumables or systems, certain assay information may be communicated to the assay system and read, write or erased locally via the identifier/controller on the assay system. For example, recall and/or license information may be a subset of assay information that is available via the network connections, whereas additional assay information e.g., lot-specific, expiration date, calibration data, consumable specific information, assay domain information, assay results information, consumable security information, or combinations thereof, may be stored locally on the identifier and otherwise unavailable via the network connections on the assay system. In one embodiment, recall, license and/or consumable security information may be available via the network connections on the assay system and the remaining assay information is stored locally on the identifier. The assay system or reader includes system hardware, system firmware, system data acquisition and control software, and method or consumable data. In various embodiments, the system hardware includes electronic control and data processing circuitry, such as a microprocessor or microcontroller, memory, and non-volatile storage. In various embodiments, the system hardware also includes physical devices to manipulate biological reagents such as robotics and sample pumps. In various embodiments, the system firmware includes low-level, computer-readable instructions for carrying out basic operations in connection with the system hardware. In various embodiments, the system firmware includes microprocessor instructions for initializing operations on a microprocessor in the system hardware.

The system data acquisition and control software is higher-level software that interfaces with the system firmware to control the system hardware for more specific operations such as operating a charge coupled device (CCD) to acquire visual luminescence information regarding a particular biological analysis. In various embodiments the data acquisition and control software includes a software-implemented state machine providing, for example, the following states: (i) idle; (ii) running; (iii) paused; and (iv) error. In various embodiments, when the state machine is in the idle state, it can receive an instruction from the general purpose machine to perform a particular data acquisition or system control operation. In various embodiments, the general purpose computer opens a TCP/IP socket connection to the system, determines whether the system is in the idle state and then begins transmitting instructions and/or parameters. In various embodiments, an encrypted TCP/IP connection is established, using, for example, the SSH protocol. The instructions and/or parameters can be in the form of ASCII encoded, human readable consumable and/or method information that defines the behavior of the biological system. In various embodiments, the consumables and/or methods are stored in the form of ASCII text files. In various embodiments, the general purpose computer uses the FTP protocol to transfer the ASCII text files to the system. In various other embodiments the method and/or consumable information is stored in and read from the identifier. The method and/or consumable information can be stored in the form of an ASCII text file in the identifier, but it is understood that the information can be represented in other data formats without departing from the present teachings.

According to various embodiments, the consumable, macro, and/or method information includes parameters that can be used by the system data acquisition and control software to perform specific data acquisition and system control operations. In various embodiments, the method and/or consumable information contains sequences of operations to be performed by the system or control parameters for use in connection with the data acquisition or control software. In one specific embodiment, the assay consumable is a cartridge as described herein above. The cartridge is provided with a consumable identifier, e.g., a memory card (which is supplied with the packaging for the cartridge or a set of a plurality of cartridges) that includes assay information, e.g., lot information and/or lot specific parameters. Prior to running an assay using a cartridge from a new lot of cartridges, the user inserts the memory card into the reader and uploads the assay information to the reader's internal memory. The cartridge also includes an additional consumable identifier, e.g., a bar code, with the cartridge lot identifier stored thereon. Al the beginning of an assay, the reader loads the cartridge and reads the cartridge lot identifier from the cartridge barcode using its internal barcode reader. The reader determines if it has lot specific information stored for that lot identifier. Then the reader reads the expiration date from the lot-specific parameters stored in its internal memory and rejects the cartridge if the on-board clock is past the expiration date. The reader executes the assay protocol and determines results based on the lot specific parameters.

In an alternate embodiment, the assay system uses a plurality of different assay consumables, e.g., one or more multi-well assay plates, one or more sample tube racks, and/or containers for assay reagents. Certain of the consumables used in the system may be associated with an identifier and others may not. In one embodiment, each consumable is associated with an identifier. In one specific embodiment of the invention, an assay consumable used in the system includes an EEPROM or RFD as a consumable identifier and the assay system includes a corresponding EEPROM or MD controller. The controller detects and uploads the data stored on the identifier and the system optionally adjusts one or more assay parameters based on the data uploaded from the identifier. Once the assay is completed, the identifier controller writes information to the identifier concerning that assay or the use of that consumable in the system. The instrument is programmed to reject any consumable that does not have a readable identifier.

The system will prompt the user to scan the reagent identifiers and will record the scanned information. The system will also prompt the user to scan the controls, calibrator and reagent identifiers and record the scanned information. The system will persistently track the consumable state so that state can be maintained in the case of a power loss or unexpected shutdown. The system will estimate the volume of fluids in the reagent bottles and it will estimate reagent consumption. The system will record the user identification for the user and that assay information will be written to the identifier. The system will also record/read the timestamp when an assay is run to the identifier and it will allow the user to enter and modify a free text comment before, during or after the assay is processed, which is also written to the identifier. The user will input sample identification for each sample and that assay information is also written to the identifier.

In a further embodiment, the assay system uses a plurality of different assay consumables, e.g., one or more multi-well assay plates, one or more sample tube racks, and/or containers for assay reagents. A single assay consumable used in the system may include a plurality of consumable identifiers, e.g., a first identifier that includes information that pertains to the entire consumable and one or more additional consumable identifiers of the same or different type that includes information that pertains to a component of that consumable. For example, if the assay consumable is a sample tube rack, the consumable includes an EEPROM or MD with information specific for the entire rack, e.g., lot information and/or lot specific parameters for the rack. The sample tube rack may also include two or more additional identifiers, e.g., a barcode, with information specific for individual samples and/or positions within the rack, e.g., information concerning the sample present at a given position in the rack. In addition, the additional identifier may be used by the system to identify the presence or absence of a sample or reagent in a given position within the rack, e.g., if the additional identifier is obscured and cannot be read by the system, the sample or reagent is present in the rack and if the additional identifier is read by the system, the sample or reagent is not present.

For each type of consumable identifier used by the assay system there is a corresponding identifier controller. For example, if the system uses a multi-well assay plate with an EEPROM identifier and a container for assay reagents with a barcode, then the system will include an EEPROM controller and a barcode controller. Each controller detects and uploads the data stored on a given identifier and the system optionally adjusts one or more assay parameters based on the data uploaded from that identifier. Once the assay is completed, the identifier controller writes information to the identifier concerning that assay or the use of that consumable in the system. The instrument is programmed to reject any consumable that does not have a readable identifier.

The system will prompt the user to scan the reagent identifiers and will record the scanned information. The system will prompt the user to scan the controls, calibrator and reagent identifiers and record the scanned information. The system will persistently track the consumable state so that state can be maintained in the case of a power loss or unexpected shutdown. The system will estimate the volume of fluids in the reagent bottles and it will estimate reagent consumption.

In one specific embodiment, the invention provides an assay system configured to use an assay cartridge in the conduct of an assay, wherein the assay system comprises a reader adapted to perform the following operations (i) reading cartridge lot identification information from a first consumable identifier associated with the assay consumable; (ii) reading lot specific parameters from an additional consumable identifier; (iii) using the lot identification information and the lot specific parameters to adjust one or more operations performed by the assay system before, during and/or after the conduct of an assay by the system. In this embodiment, the lot specific parameters are selected from the group consisting of (i) a revision level that determines schema used to interpret assay results and/or assay information; (ii) cartridge type; (iii) year of cartridge manufacture; (iv) cartridge lot number; (v) expiration date of cartridge and/or reagents used in the assay; (vi) a cross-talk correction matrix to account for chemical cross-reactivity; (vi) threshold values for assays to be conducted in the cartridge; (vii) a range for internal positive control(s) used in the assay;

a ranges for each assay to be conducted in the cartridge for a positive control sample; and (ix) a software checksum. The first consumable identifier comprises non-volatile memory, e.g., an RFID tag, a bar code, ICC, an EPROM, and EEPROM. In one embodiment, the non-volatile memory is a bar code. The additional consumable identifier also comprises non-volatile memory, e.g., an RFID tag, a bar code, ICC, an EPROM, and EEPROM. In one embodiment, the additional consumable identifier is an ICC, e.g., a memory card.

Therefore, an assay procedure using an assay consumable cartridge in an assay system, e.g., an assay reader, includes inserting the cartridge in the reader to allow the identifier controller to interact with the identifier affixed to or associated with the cartridge. Alternatively, the cartridge packaging includes the identifier affixed thereto or associated therewith and before the cartridge is inserted into the reader, the identifier of the cartridge packaging is contacted with the identifier controller. The identifier controller associated with the reader reads the cartridge lot identification information from the first consumable identifier as well as the lot specific parameters from any additional consumable identifier. The reader then uses the lot identification information and the lot specific parameters to adjust one or more operations performed by the reader before, during and/or after the conduct of an assay. For each lot specific parameter, the reader may adjust the system or output accordingly. Thereafter, the reader makes the appropriate electrical, fluidic and/or optical connections to the cartridge (making use of electrical, fluidic and/or optical connectors on the cartridge and reader) and conducts an assay in the cartridge. The sample may be introduced into the cartridge prior to inserting the cartridge in the reader. The assay may also involve adding one or more assay reagents to the cartridge and instructions for adding those various assay reagents may be saved to the identifier and the reader adds those reagents to the cartridge before or during the assay according to the instructions saved to the assay consumable identifier.

In another specific embodiment, the invention provides an assay system configured to use a multi-well assay plate, an additional multi-well assay plate (referred to as an auxiliary plate), and one or more sample tube racks in the conduct of an assay, wherein the assay system comprises a reader adapted to perform one or more of the following operations (i) reading tube position information from a first consumable identifier associated with the one or more sample tube racks; (ii) reading assay information and lot specific parameters from an additional consumable identifier associated with the auxiliary plate; (iii) using position information and lot specific parameters to adjust one or more operations performed by the assay system before, during and/or after the conduct of an assay using the multi-well assay plate and the auxiliary plate; (iv) erasing information from a consumable identifier; and (v) writing information to a consumable identifier. In one embodiment, the assay information is selected from the group consisting of (i) a digital signature to verify manufacturer identify; (ii) lot code of the multi-well assay plate and/or the auxiliary plate; (iii) expiration date of the multi-well assay plate and/or the auxiliary plate; (iv) type of multi-well assay plate and/or the auxiliary plate; (v) serialized identification for the auxiliary plate; and (vi) lot specific parameters for the multi-well assay plate and/or the auxiliary plate. Still further, the lot specific parameters for the multi-well assay plate are selected. from the group consisting of (i) in-well control acceptance ranges; (ii) assay names; (iii) assay identifiers; (iv) assay thresholds; (v) number and identity of assay quality controls; (vi) assay quality control acceptance ranges; (vii) calibration information; (viii) number and identity of assay calibrators; (ix) assay calibrator acceptance ranges; (x) chemical cross-talk matrix for the multi-well assay plate; and (xi) combinations thereof. The first consumable identifier may comprise non-volatile memory, e.g., an RFID tag, a bar code, ICC, an EPROM, and EEPROM. In one embodiment, the non-volatile memory is a bar code. The additional consumable identifier comprises non-volatile memory, e.g., an RFID tag, a bar code, ICC, an EPROM, and EEPROM. In one embodiment, the additional consumable identifier is an EEPROM or an RFID.

Reference is made to copending U.S. Provisional Patent Application Ser. No. 61/271,874, filed Jul. 27, 2009, the disclosure of which is incorporated herein by reference. In one embodiment, a method of using such an assay system includes (a) introducing a sample tube rack into a sample rack subassembly; (b) reading sample and assay-specific information from the identifiers on the sample rack subassembly and/or reading sample and assay-specific information manually input into the computer user interface by the user; (c) introducing an auxiliary plate to an auxiliary plate subassembly; (d) reading assay-specific information from the identifiers on the auxiliary plate; (e) introducing an assay test plate into a plate introduction aperture of a light-tight enclosure of the apparatus; (f) reading assay-specific information from the identifiers on the assay test plate; (g) sealing the door of the plate introduction aperture, (f) translating the test plate to position one or more wells under a light detector, (g) rehydrating reagents in one or more auxiliary wells of the auxiliary plate using a pipetting arm subassembly and/or pretreating one or more wells of the test plate using the pipetting arm subassembly; (h) collecting a sample volume from a sample tube of the sample rack subassembly and pipetting that sample volume into a well of an assay test plate; (i) collecting sample reagents from the auxiliary plate and dispensing those reagents into a well of the assay test plate; (j) detecting luminescence from the one or more wells, (k) repeating one or more of the preceding steps on additional wells of the test plate, using additional auxiliary wells of the auxiliary plate; (j) translating the used test plate to a plate elevator; (k) raising the plate elevator; and (l) removing the test plate from the plate introduction aperture.

The method may also, optionally, comprise one or more of: i) pre-treating sample and/or reagent in a auxiliary well of the auxiliary plate and pipetting that pre-treated sample and/or reagent into or out of one of a auxiliary well of a test plate; ii) removing seals from one or more of the auxiliary wells and/or wells of the auxiliary plate and/or test plate, respectively, or iii) applying electrical energy to electrodes in one or more of said test plate wells (e.g., to induce electrochemiluminescence).

One assay procedure using an assay consumable, e.g., a multi-domain multi-well plate, and an assay system would comprise inserting the consumable in the system to allow the identifier controller to interact with the identifier affixed to or associated with the consumable. Alternatively, the consumable packaging includes the identifier affixed thereto or associated therewith and before the consumable is inserted into the system, the identifier associated with the consumable packaging is contacted with the identifier controller. The system may adjust the assay parameters prior to initiating an assay based on the assay information saved to the identifier. Thereafter, the system makes the appropriate electrical, fluidic and/or optical connections to the consumable (making use of electrical, fluidic and/or optical connectors on the consumable and system) and conducts an assay using the consumable. The sample may be introduced into the consumable prior to inserting the consumable in the system. Alternatively, the sample is introduced by a component of the system after the consumable is inserted in the system. The assay may also involve adding one or more assay reagents to the consumable and instructions for adding those various assay reagents may be saved to the identifier and the system adds those reagents to the consumable before or during the assay according to the instructions saved to the assay consumable identifier.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. A method of using an assay cartridge, in the conduct of an assay, with an assay system, said assay system comprising a reader, the method comprising:
   (i) reading cartridge lot identification information from a first consumable identifier associated with an assay consumable;
   (ii) reading lot specific parameters from an additional consumable identifier;
   (iii) performing an operation selected from the group consisting of (i) read information from said consumable identifier; (ii) erase information from said consumable identifier; (iii) write information to said consumable identifier; and (iv) combinations thereof, wherein said read information, erase information, and/or write information comprises:
   authorization information for said consumable or a test site thereof or a domain thereof, said authorization information comprising whether a user has a valid license to use said consumable, the number of times the user is permitted to use said consumable, or the limitations on said use of the consumable by the user, if any, and at least one of the following (a)-(c);
   (a) a digital signature indicating the consumable was manufactured by a designated vendor;
   (b) data regarding how one or more steps in an assay protocol may be adjusted to account for lot to lot or consumable to consumable differences; or
   (c) lot-specific analysis parameters comprising the revision level that determines the schema used to interpret the assay results, a cross-talk correction matrix to account for chemical cross-reactivity, a threshold for assays to be conducted in the consumable and each internal negative control, a range for each internal positive control, ranges for each assay to be conducted for the positive control sample, a software checksum to ensure integrity of the data, in-well or in-test site control acceptance ranges, negative and positive quality control materials that are used to verify the operation of said consumable, master calibration curve information, or assay calibrator acceptance ranges, and
   (iv) using said lot identification information and said lot specific parameters to adjust one or more operations performed by said assay system before, during and/or after the conduct of an assay by said system.

2. The method of claim 1, wherein said lot specific parameters are selected from the group consisting of (i) a revision level that determines schema used to interpret assay results and/or assay information; (ii) cartridge type; (iii) year of cartridge manufacture; (iv) cartridge lot number; (v) expiration date of cartridge and/or reagents used in said assay; (vi) a cross-talk correction matrix to account for chemical cross-reactivity; (vi) threshold values for assays to be conducted in said cartridge; (vii) a range for internal positive control(s) used in said assay; (viii) a ranges for each assay to be conducted in said cartridge for a positive control sample; and (ix) a software checksum.

3. The method of claim 1, wherein said first consumable identifier comprises non-volatile memory.

4. The method of claim 3, wherein said non-volatile memory is selected from the group consisting of an RFID tag, a bar code, ICC, an EPROM, and EEPROM.

5. The method of claim 4, wherein said non-volatile memory is a bar code.

6. The method of claim 1, wherein said additional consumable identifier comprises non-volatile memory.

7. The method of claim 6, wherein said non-volatile memory is selected from the group consisting of an RFID tag, a bar code, ICC, an EPROM, and EEPROM.

8. The method of claim 7, wherein said non-volatile memory is an ICC.

9. The method of claim 8, wherein said ICC is a memory card.

10. A computer readable medium having stored thereon a computer program which, when executed by a computer system, causes the computer system to perform a method of using an assay cartridge, in the conduct of an assay, with an assay system, said assay system comprising a reader, the method comprising:
    (i) reading cartridge lot identification information from a first consumable identifier associated with an assay consumable;
    (ii) reading lot specific parameters from an additional consumable identifier;
    (iii) performing an operation selected from the group consisting of (i) read information from said consumable identifier; (ii) erase information from said consumable identifier; (iii) write information to said consumable identifier; and (iv) combinations thereof, wherein said read information, erase information, and/or write information comprises:
    authorization information for said consumable or a test site thereof or a domain thereof, said authorization information comprising whether a user has a valid license to use said consumable, the number of times the user is permitted to use said consumable, or the limitations on said use of the consumable by the user, if any, and at least one of the following (a)-(c);
    (a) a digital signature indicating the consumable was manufactured by a designated vendor;
    (b) data regarding how one or more steps in an assay protocol may be adjusted to account for lot to lot or consumable to consumable differences; or
    (c) lot-specific analysis parameters comprising the revision level that determines the schema used to interpret the assay results, a cross-talk correction matrix to account for chemical cross-reactivity, a threshold for assays to be conducted in the consumable and each internal negative control, a range for each internal positive control, ranges for each assay to be conducted for the positive control sample, a software checksum to ensure integrity of the data, in-well or in-test site control acceptance ranges, negative and positive quality control materials that are used to verify the operation of said consumable, master calibration curve information, or assay calibrator acceptance ranges, and
    (iv) using said lot identification information and said lot specific parameters to adjust one or more operations performed by said assay system before, during and/or after the conduct of an assay by said assay system.

11. The computer readable medium of claim 10, wherein said lot specific parameters are selected from the group consisting of (i) a revision level that determines schema used to interpret assay results and/or assay information; (ii) cartridge type; (iii) year of cartridge manufacture; (iv) cartridge lot number; (v) expiration date of cartridge and/or reagents used in said assay; (vi) a cross-talk correction matrix to account for chemical cross-reactivity; (vi) threshold values for assays to be conducted in said cartridge; (vii) a range for internal positive control(s) used in said assay; (viii) a ranges for each assay to be conducted in said cartridge for a positive control sample; and (ix) a software checksum.

12. The computer readable medium of claim 10, wherein said first consumable identifier comprises non-volatile memory.

13. The computer readable medium of claim 12, wherein said non-volatile memory is selected from the group consisting of an RFID tag, a bar code, ICC, an EPROM, and EEPROM.

14. The computer readable medium of claim 13, wherein said non-volatile memory is a bar code.

15. The computer readable medium of claim 10, wherein said additional consumable identifier comprises non-volatile memory.

16. The computer readable medium of claim 15, wherein said non-volatile memory is selected from the group consisting of an RFID tag, a bar code, ICC, an EPROM, and EEPROM.

17. The computer readable medium of claim 16, wherein said non-volatile memory is an ICC.

18. The computer readable medium of claim 17, wherein said ICC is a memory card.

19. The method of claim 1, wherein the assay system further comprises an auxiliary assay plate, wherein said auxiliary assay plate comprises an auxiliary assay consumable identifier, wherein said reader is adapted to perform an operation of reading information from said auxiliary assay consumable identifier.

20. The method of claim 19, wherein said auxiliary assay consumable identifier comprises information identifying the auxiliary assay plate.

21. The method of claim 20, wherein said auxiliary assay consumable identifier is a barcode.

22. The method of claim 1, wherein the first consumable identifier further comprises origin information regarding the origin of a biological reagent used in the assay consumable, the origin information comprising identification of an original sample from which it was derived and the number of generations removed it is from an original sample.

23. The computer readable medium of claim 10, wherein the assay system further comprises an auxiliary assay plate, wherein said auxiliary assay plate comprises an auxiliary assay consumable identifier, wherein said reader is adapted to perform an operation of reading information from said auxiliary assay consumable identifier.

24. The computer readable medium of claim 23, wherein said auxiliary assay consumable identifier comprises information identifying the auxiliary assay plate.

25. The computer readable medium of claim 24, wherein said auxiliary assay consumable identifier is a barcode.

26. The computer readable medium of claim 10, wherein the first consumable identifier further comprises origin information regarding the origin of a biological reagent used in the assay consumable, the origin information comprising identification of an original sample from which it was derived and the number of generations removed it is from an original sample.

27. The method of claim 1, wherein said read information, erase information, and/or write information further comprises:
lot-specific analysis parameters comprising the revision level that determines the schema used to interpret the assay results, a cross-talk correction matrix to account for chemical cross-reactivity, a threshold for assays to be conducted in the consumable and each internal negative control, a range for each internal positive control, ranges for each assay to be conducted for the positive control sample, a software checksum to ensure integrity of the data, in-well or in-test site control acceptance ranges, negative and positive quality control materials that are used to verify the operation of said consumable, master calibration curve information, or assay calibrator acceptance ranges.

28. The computer readable medium of claim 10, wherein said read information, erase information, and/or write information further comprises:
lot-specific analysis parameters comprising the revision level that determines the schema used to interpret the assay results, a cross-talk correction matrix to account for chemical cross-reactivity, a threshold for assays to be conducted in the consumable and each internal negative control, a range for each internal positive control, ranges for each assay to be conducted for the positive control sample, a software checksum to ensure integrity of the data, in-well or in-test site control acceptance ranges, negative and positive quality control materials that are used to verify the operation of said consumable, master calibration curve information, or assay calibrator acceptance ranges.

\* \* \* \* \*